(12) United States Patent
Ely et al.

(10) Patent No.: US 11,590,495 B2
(45) Date of Patent: Feb. 28, 2023

(54) IONIC SPECIES INTERROGATION AND SENSING

(71) Applicant: HEWLETT-PACKARD DEVELOPMENT COMPANY, L.P., Spring, TX (US)

(72) Inventors: Hilary Ely, Corvallis, OR (US); Matthew David Smith, Corvallis, OR (US); Jeremy Sells, Corvallis, OR (US); George H. Corrigan, Corvallis, OR (US); Michael W. Cumbie, Corvallis, OR (US); Chantelle Domingue, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 438 days.

(21) Appl. No.: 16/619,508

(22) PCT Filed: Jul. 28, 2017

(86) PCT No.: PCT/US2017/044314
§ 371 (c)(1),
(2) Date: Dec. 5, 2019

(87) PCT Pub. No.: WO2019/022753
PCT Pub. Date: Jan. 31, 2019

(65) Prior Publication Data
US 2020/0197936 A1 Jun. 25, 2020

(51) Int. Cl.
*C12Q 1/6876* (2018.01)
*B01L 3/00* (2006.01)
(Continued)

(52) U.S. Cl.
CPC ........... *B01L 3/502715* (2013.01); *B01L 7/52* (2013.01); *C12Q 1/6876* (2013.01);
(Continued)

(58) Field of Classification Search
CPC ............ G01N 2021/7786; G01N 21/78; B01L 3/502715; B01L 7/00; B01L 7/52; C12Q 1/6844; C12Q 1/6876
See application file for complete search history.

(56) References Cited

U.S. PATENT DOCUMENTS 8,431,389 B2    4/2013    Battrell et al.
8,507,208 B2    8/2013    Corcoran et al.
(Continued)

FOREIGN PATENT DOCUMENTS

RU           2532853 C2    11/2014
WO    WO-2010019898 A1    2/2010
(Continued)

OTHER PUBLICATIONS

Cady et al., "Real-time PCR detection of Listeria monocytogenes using an integrated microfluidic platform," Sensors and Actuators B, vol. 107, pp. 332-341. (Year: 2005).*
(Continued)

*Primary Examiner* — Young J Kim
(74) *Attorney, Agent, or Firm* — Foley & Lardner LLP

(57) ABSTRACT

A method may include maintaining a sample comprising an ionic species and an optical indicator at an elevated temperature above 25° C. on a semi-conductive microfluidic die during an incubation period, intermittently interrogating the sample with an interrogating light during the incubation period and sensing a response of the sample to the interrogating light, wherein the sample is interrogated with the interrogating light only during those times at which the sample is being sensed.

15 Claims, 5 Drawing Sheets

(51) Int. Cl.
*B01L 7/00* (2006.01)
*G01N 21/64* (2006.01)
(52) U.S. Cl.
CPC .... G01N 21/6408 (2013.01); *B01L 2300/046* (2013.01); *B01L 2300/06* (2013.01); *B01L 2300/0627* (2013.01); *B01L 2300/12* (2013.01); *B01L 2300/1805* (2013.01)

(56) References Cited

U.S. PATENT DOCUMENTS

| | | | | |
|---|---|---|---|---|
| 2006/0078475 | A1* | 4/2006 | Tai | B01L 9/527 |
| | | | | 422/400 |
| 2007/0059754 | A1* | 3/2007 | Kordunsky | G01N 21/276 |
| | | | | 435/287.2 |
| 2014/0005066 | A1* | 1/2014 | Boles | C12Q 1/686 |
| | | | | 506/9 |

FOREIGN PATENT DOCUMENTS

| | | |
|---|---|---|
| WO | WO-2011156847 A1 | 12/2011 |
| WO | WO-2014028378 A2 | 2/2014 |

OTHER PUBLICATIONS

Merriam-Webster on-line dictionary definition of "Pulsate", [retrieved on-line, retrieval date, Jul. 13, 2022; retrieved from:https://www.merriam-webster.com/dictionary/pulsate].*

Troger, V. et al., Isothermal Amplification and Quantification of Nucleic Acids and Its Use in Microsystems, Apr. 10, 2015 <https://www.omicsonline.org/open-access/isothermal-amplification-and-quantification-of-nucleic-acids-and-its-usein-microsystems-2157-7439-1000282.php?aid-51731 >.

Zhang, C et al., Miniaturized PCR Chips for Nucleic Acid Amplification and Analysis: Latest Advances and Future Trends, Jun. 18, 2007, < https://www.ncbi.nlm.nih.gov/pmc/articles/PMC1934988/>.

* cited by examiner

US 11,590,495 B2

IONIC SPECIES INTERROGATION AND SENSING

BACKGROUND

Tests are sometimes carried out on samples to determine the presence or absence of an ionic species to identify a state of the sample source. For example, nucleic acid tests are sometimes carried out to determine the presence or absence of an ionic species such as deoxyribonucleic acid (DNA) or ribonucleic acid (RNA) to determine various states of health or disease of the organism from which the sample was taken. Such a test may be part of a screening assay in the field or at the point of care by clinicians.

Figure 1:
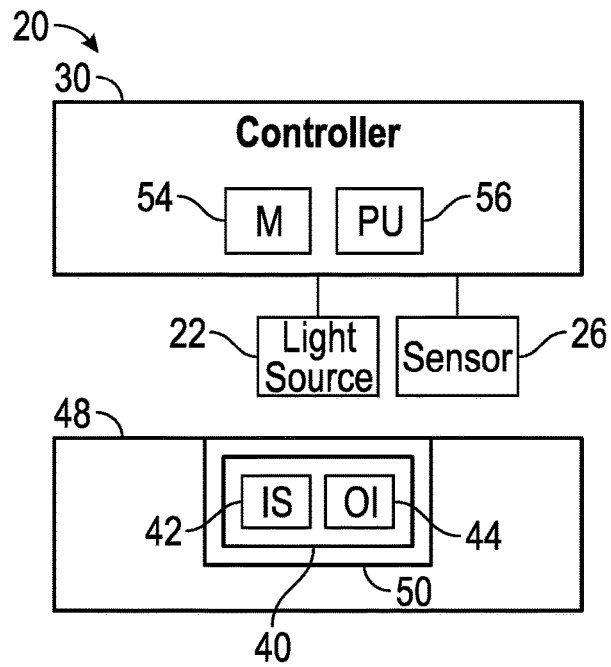
FIG. 1 is a schematic diagram of portions of an example ionic species interrogation and sensing system.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION OF EXAMPLES

Tests are sometimes carried out on samples to determine the presence or absence of an ionic species to identify a state of the sample source. For example, nucleic acid tests are sometimes carried out to determine the presence or absence of a targeted ionic species such as deoxyribonucleic acid (DNA) or ribonucleic acid (RNA) to determine various states of health or disease of the organism from which the sample was taken. During such testing, biochemical reactions are carried out on the sample to multiply any existing selected ionic species in the sample, wherein the ionic species, if present, attains a population sufficient to output a certain response to light interrogation. In some circumstances, the time for the ionic species to attain the population sufficient to output a certain response to light interrogation may indicate the degree to which the ionic species is present in the source of the sample.

The testing for the presence of a particular targeted ionic species is often carried out in a laboratory on a relatively large scale, utilizing relatively large samples and expensive testing equipment. Performing ionic species presence testing, such as nucleic acid testing, on a smaller scale, such as a microfluidic scale to reduce sample size and reduce cost presents many challenges. Many microfluidic devices, such as microfluidic dies often utilized in lab on chip applications, employ semi conductive materials, such as silicon. Unfortunately, it has been discovered that such semiconductive materials, when maintained at an elevated temperature and when subjected to the light used to interrogate the sample may free electrons that may alter the ionic environment containing or supporting the sample being tested. The altered ionic environment may detrimentally impact the reliability of the test, potentially producing false positives or false negatives. Such false positives or false negatives may result in an incorrect diagnosis regarding the state of health or disease of the organism from which the tested sample was taken.

Disclosed herein are example methods for testing for the presence or absence of target ionic species using a microfluidic device or microfluidic die, wherein the methods provide enhanced control over the ionic environment of the sample being tested to enhance the reliability of the tests. Disclosed herein are example ionic species interrogation and sensing systems that carry out testing for the presence or absence of target ionic species using a microfluidic device while providing enhanced control over the ionic environment of the sample being tested to enhance the reliability of the tests.

The example methods and systems intermittently or non-continuously interrogate the sample on the microfluidic device or microfluidic die with interrogation light during the incubation period in which the sample undergoes multiplication processes. The intermittent interrogation of the sample with light may begin at the beginning of incubation, the period of time during which the sample is at an elevated temperature and in the presence of a reaction catalyst. In other implementations, the intermittent interrogation of the sample may begin at a predefined time following the initiation of the incubation period. In some implementations, such intermittent interrogation of the sample with light and sensing of an optical response of the sample to the interrogating light continues during the incubation period until the end of the incubation period or until the optical response of the sample during the incubation period satisfies a predetermined threshold, confirming the presence of the targeted ionic species in the sample. If the optical response does not satisfy the predetermined threshold during the incubation period, it may be determined that the sample lacks the targeted ionic species.

In one implementation, the sample is intermittently sensed during the incubation time period, wherein the intermittent sensing corresponds to the intermittent interrogation of the sample with light. The intermittent sensing and intermittent interrogation may begin at the beginning of the incubation time period or may begin at a predefined time following the initiation of incubation. Once started, the intermittent sensing and intermittent interrogation may continue until the first of either the end of the incubation period or the optical response of the sample during the incubation period satisfying a predetermined threshold, confirming the presence of the targeted ionic species in the sample.

The sample is interrogated or impinged with light only during those times at which an optical response of the sample to the interrogating light is sensed. In one implementation, the intermittent interrogating of the sample has a duty cycle of less than 40%. By reducing exposure of the semi conductive microfluidic device or die to the interrogating light, the number of free electrons are reduced and the ionic environment of the sample being tested is more controlled to potentially achieve more reliable testing results.

In some implementations, the sample (given the optical indicator, the reaction catalyst and the targeted ionic species for which the presence or absence of which is being determined) may be expected to have a predetermined breakthrough time. The predetermined expected breakthrough time is a point in time during the period of incubation at which the ionic species, if present, will have been multiplied or amplified to a sufficient extent so as to produce an optical response upon being interrogated that exceeds a predefined threshold used to indicate the presence of the ionic species in the sample. In such an implementation, the frequency at which the sample is intermittently interrogated with light to produce the optical response, based in part upon the optical indicator, is varied based upon the predetermined anticipated or expected breakthrough time. For example, during a window of time containing the expected breakthrough time, the sample may be interrogated with light at a first frequency that is greater than a second frequency at which the samples interrogated at other times outside the window.

The time during the period of incubation for the sample at which the optical response of the sample achieves breakthrough, exceeding the threshold, may often indicate not only the presence or absence of the targeted ionic species, but also in extent or degree to which the ionic species may be present in the sample, and present in the host from which the sample was taken. For example, a sample which achieves "breakthrough" earlier may be determined to have a greater extent of the targeted ionic species as compared to a different sample which achieves the same breakthrough later in time during the incubation period. Of course, sample which is not achieved breakthrough may be determined to not contain the targeted ionic species.

By interrogating the sample with light at a greater frequency during the window of time containing the expected breakthrough time, a greater resolution for the actual breakthrough time may be achieved. At the same time, by interrogating the sample with light at the lower first frequency during those interrogation times outside of the window, the sample, and the microfluidic die supporting the sample, are subjected to less light, reducing the number of free electrons that may be produced by the semiconductive material and providing more stability or control over the ionic environment of the sample being tested.

Disclosed herein are example ionic species interrogation and sensing system that provide further enhanced control over the ionic environment of the sample being tested by further inhibiting ambient light from impinging the semiconductive microfluidic die and the contained sample. In one implementation, the microfluidic die and the supported sample may be inserted into a light blocking chamber that encompasses the microfluidic die, the light source and the sensor. In another implementation, the Mike fluidic die in the supported sample may be inserted into a light blocking case or chamber that encompasses the controller (and potentially the heater) as well. As with the other implementations, the sample, within the chamber, is intermittently interrogated with light from the light source during the incubation time.

Some example microfluidic devices or microfluidic dies may comprise microfluidic channels. Microfluidic channels may be formed by performing etching, microfabrication (e.g., photolithography), micromachining processes, or any combination thereof in a substrate of the fluidic die. Accordingly, microfluidic channels, chambers, orifices, and/or other such features may be defined by surfaces fabricated in the substrate of a fluidic die. Furthermore, as used herein a microfluidic channel may correspond to a channel of sufficiently small size (e.g., of nanometer sized scale, micrometer sized scale, millimeter sized scale, etc.) to facilitate conveyance of small volumes of fluid (e.g., picoliter scale, nanoliter scale, microliter scale, milliliter scale, etc.).

Disclosed herein is an example method that may include maintaining a sample comprising an ionic species and an optical indicator at an elevated temperature above 25° C. on a semi-conductive microfluidic die during an incubation period, intermittently interrogating the sample with an interrogating light during the incubation period and sensing a response of the sample to the interrogating light only during those times at which the sample is being interrogated with the interrogating light.

Disclosed herein is an example method that may include maintaining a sample comprising an ionic species and an optical indicator at an elevated temperature above 25° C. on a semi-conductive microfluidic die during an incubation period, intermittently interrogating the sample with an interrogating light during the incubation period, wherein the intermittent interrogating of the sample has a duty cycle of less than 40% and sensing a response of the sample to the interrogating light during those times at which the sample is being interrogated with the interrogating light.

Disclosed herein is an example ionic species interrogation and sensing system that may include a light source and a controller to output control signals causing the light source to intermittently interrogate a sample of an ionic species and an optical indicator on a semiconductive microfluidic die with an interrogating light during an incubation period during which the sample is at an elevated temperature above 25° C. The intermittent interrogating of the sample has a duty cycle of less than 40%.

FIG. 1 is a schematic diagram of portions of an example ionic species interrogation and sensing system 20. System 20 facilitates the interrogation and sensing of a sample 40 supported on a microfluidic die 48 at least partially formed from a semiconductive material. The sample 40 comprises an ionic species 42, the presence of which is to be confirmed and/or measured, and an optical indicator 44. Ionic species comprise biochemistries that produce ionic byproducts when being multiplied or amplified. One example of an ionic species are nucleic acids such as DNA and RNA. Sample 40 may additionally comprise other components such as reaction catalyst last reagents that facilitate amplification or multiplication of any targeted ionic species that may be present.

Optical indicator 44 comprises at least one chemical added and mixed with the ionic species, wherein the optical indicator optically indicates, to an optical sensor, the presence of the targeted ionic species or the ionic byproducts produced by the ionic species during its multiplication or amplification. The optical indicator may target selected ionic byproducts and/or selected ionic species that produce the specific ionic byproducts. As a result, different optic indicators may be utilized to detect the presence of different targeted ionic species.

In one implementation, the optical indicator 44 may comprise a fluorescent probe or fluorophore that, in response to an excitation light source and while directly interacting with the ionic species or its ionic byproducts, change in fluorescence. One type of fluorophore begins to fluoresce or increases in its level of fluorescence in response to an excitation light source and direct interaction with a target ionic species and/or the ionic byproduct of the target ionic species. In such implementations, sample 40 may additionally include various ions associated with the fluorophore. Examples of fluorophores include, but are not limited to, Calcein, Fluorescein, EvaGreen®, SYBR® Green, SYTO™-X, or any other fluorescent indicator useful in either real time or endpoint optical detection of nucleic acid amplification.

Another type of fluorophore stops fluorescing or decreases its level of fluorescence in response to an excitation light source while directly interacting with the targeted ionic species and/or the ionic byproduct of the targeted ionic species. In such implementations, sample 40 may additionally include various ions associated with the fluorophore. Examples of such fluorophores include, but are not limited to, Methylene Blue. In such implementations, the fluorophore optical indicator, in response to being impinged by an excitation light source provided by an interrogating light from a light source, provides a level of fluorescence that may be sensed by an optical sensor to indicate the presence of the targeted ionic species either directly or as inferred from the detected presence of the ionic byproducts of the targeted ionic species.

In another implementation, the optical indicator may comprise a dye that, in in response to interacting directly with the targeted ionic species or the ionic byproducts of the targeted ionic species, changes in color, changes its properties with respect to absorbing an interrogation light from an excitation light source. In such an implementation, an interrogation light is directed at the sample 40 with the dye, wherein the dye differently absorbs selected wavelengths of light in response to directly interacting with the targeted ionic species or its ionic byproducts. The wavelengths of light not absorbed by the dye (the color of the sample) are sensed to indicate the presence of the targeted ionic species either directly or as inferred from the detected presence of the ionic byproducts of the targeted ionic species. Examples of such optic indicators in the form of a dye include, but are not limited to, Hydroxynaphthol Blue.

As further shown by FIG. 1, sample 40 is supported by a microfluidic die 48. The microfluidic die 48 is at least partially formed from a semiconductive material that produces free electrons when at an elevated temperature, a temperature above room temperature, above 25° C., and when impinged or excited by a light. One example of such a semiconductive material is crystalline silicon. Other examples of such semiconductor materials include, but are not limited to, Amorphous silicon, cadmium telluride, copper indium gallium selenide, or gallium arsenide thin film.

In some implementations, sample 40 is located within a microfluidic volume 50. Microfluidic volume 50 may comprise a passage through which sample 40 is allowed to flow or a reservoir containing and restricting the flow of sample 40. Microfluidic volume 50 sufficiently small size (e.g., of nanometer sized scale, micrometer sized scale, millimeter sized scale, etc.) to facilitate conveyance of small volumes of fluid (e.g., picoliter scale, nanoliter scale, microliter scale, milliliter scale, etc.).

In some implementations, microfluidic die 48 may be partially formed by semiconductive material that creates free electrons when impinged with light at an elevated temperature. For example, in some implementations, microfluidic die 48 may comprise an underlying substrate or base formed from a semiconductive material, such as silicon, wherein the microfluidic volume 50 is formed or defined by a different non-semiconductive material such as a glass, polymer, ceramic or other material. In some implementations, microfluidic volume 50 may be formed by a material that may be molded or photo patterned such as an epoxy based photo resists such as Su-8. In some implementations, microfluidic volume 50 may form from other materials such as polydimethylsiloxane (PDMS) and plastic.

System 20 comprises light source 22, sensor 26 and controller 30. Light source 22 comprises a source of light to direct a sample interrogating light or an excitation light onto sample 40. In one implementation, light source 22 continuously emits light. In another implementation, light source 22 may be selectively turned on and off or pulsed by controller 30. The wavelengths or wavelengths of light provided by light source 22 may vary depending upon the ionic species being targeted and the characteristics of the optical indicator that is targeting the ionic species. For example, in implementations where the optical indicator comprises Calcein, light source 22 may output light having a wavelength of between 400 nm (near ultraviolet) and 480 nm (blue visible light). In other implementations, light source 22 may output other wavelengths of light.

Sensor 26 comprises an optical sensor that detects the optical response of the optical indicator to the interrogating light serving as the excitation light source. For example, in those implementations in which the optical indicator 44 comprises a fluorophore, sensor 26 may have physical properties so as to sense the level or degree of fluorescence coming from sample 40 as sample 40 is being impinged by light from light source 22. In one implementation, level of fluorescence may be determined by comparing the wavelengths or intensity of the light from light source 22 to the wavelengths of light or intensity of light sensed by sensor 26. In those implementations which the optical indicator 44 comprises a dye, sensor 26 may have physical properties so as to sense the wavelength of light or color of sample 40 during interrogation by light from light source 22. The wavelengths of light being sensed are those wavelengths of light from light source 22 that are not absorbed by the dye.

Due to the relatively small size of sample 40, the ionic environment of sample 40 provided by microfluidic die 48 has an enhanced sensitivity to the free electrons that occur when the semiconductive material of microfluidic die 48 is at an elevated temperature during the amplification or multiplication of the ionic species and when the semiconductive material of the microfluidic die 48 is being impinged with light for the purpose of sensing an optical response of the optical indicator. Even in those implementations where microfluidic volume 50 is formed from a non-semiconductive material, the relatively small dimensions of microfluidic volume 50 and the resulting close proximity of the semiconductive material, may alter the ionic environment within microfluidic volume 50. Changes in the ionic environment resulting from the free electrons from the semiconductive material may alter the response of the optical indicator sensed by sensor 26, potentially resulting in an incorrect determination with regard to the presence or absence of the targeted ionic species 42.

Controller 30 provides enhanced control over the ionic environment of sample 40 by controlling light source 22 so as to intermittently interrogate or impinge sample 40 and supporting microfluidic die 48 with the interrogating light. The intermittent nature at which the semiconductive material of microfluidic die 48 is impinged with the interrogating light may reduce the presence of free electrons from the semiconductive material, reducing the degree to which the ionic environment of sample 40 is altered during testing.

In the example illustrated, controller 30 is illustrated as comprising a single controller that controls both light source 22 and sensor 26. In other implementations, the control functions of controller 30 may be distributed amongst multiple sub controllers that cooperate with one another to control individual components of system 20, such as a first sub controller to control light source 22 and a second sub controller to control sensor 26. In some implementations, controller 30 or its sub controllers may further control the temperature at which microfluidic die 48 is maintained during the multiplication or amplification of the targeted ionic species 42 in sample 40, if present.

As schematically shown by FIG. 1, controller 30 comprises memory 54 and processing unit 56. Memory 54 comprises a non-transitory computer-readable medium that contains instructions for directing processing unit 56 to carry out the control of light source 22 and sensor 26. In one implementation, memory 54 contains instructions for directing processing unit 56 to intermittently direct interrogating light and sample 40 and microfluidic die 48. In one implementation, controller 30 may intermittently drive or power light source 22 so as to intermittently interrogate sample 40 with an interrogating light during an incubation period during which the ionic species 42 of sample 40, if present, are being multiplied. In another implementation, controller 30 may control a light blocking element, such as a shutter between my fluidic die 48 and light source 22, to facilitate the intermittently interrogate sample 40 with an interrogating light from light source 22 during an incubation period during which the ionic species 42 of sample 40, if present, are being multiplied.

In one implementation, the instructions 54 direct processing unit 56 to intermittently direct light from light source 22 at sample 40 and microfluidic die 48 only during those times at which sample 40 is to be sensed by sensor 26. For example, rather than continuously illuminating sample 40 and periodically or intermittently capturing an optical response of optical indicator 44 with sensor 26, controller 30 begins directing light from light source 22 onto sample 40 just prior to or concurrently with the initiation of sensing by sensor 26 and terminates the impingement of sample 40 (and microfluidic die 48) by light from light source 22 concurrently with the termination of sensing by sensor 26 or just following the termination of sensing by sensor 26.

In another implementation, the instructions 54 direct processing unit 56 to intermittently light or interrogate sample 40 and microfluidic die 48 such that the intermittent interrogation of the sample 40 has a duty cycle of less than 40% during the incubation period of time during which the ionic species is being amplified or multiplied. In other words, powering of light source 22 or the actuation of a light blocking element or shutter may be pulsed or cycled between on/off or light blocking/light transmitting states, wherein sample 40 and microfluidic die 48 are interrogated or impinged with light from light source 22 up to 40% of the time during which the ionic species is being amplified or multiplied. In other implementations, the instructions stored in memory 54 direct processing unit 56 to intermittently light or interrogate sample 40 and microfluidic die 48 such that the intermittent interrogation of the sample 40 has a duty cycle of less than 10% during the incubation period of time during which the ionic species is being amplified or multiplied. The reduced time during which sample 40 and microfluidic die 48 is interrogated or impinged with interrogating light results in a reduction in free electrons, providing enhanced control or stability for the ionic environment provided to sample 40 during testing.

Figure 2:
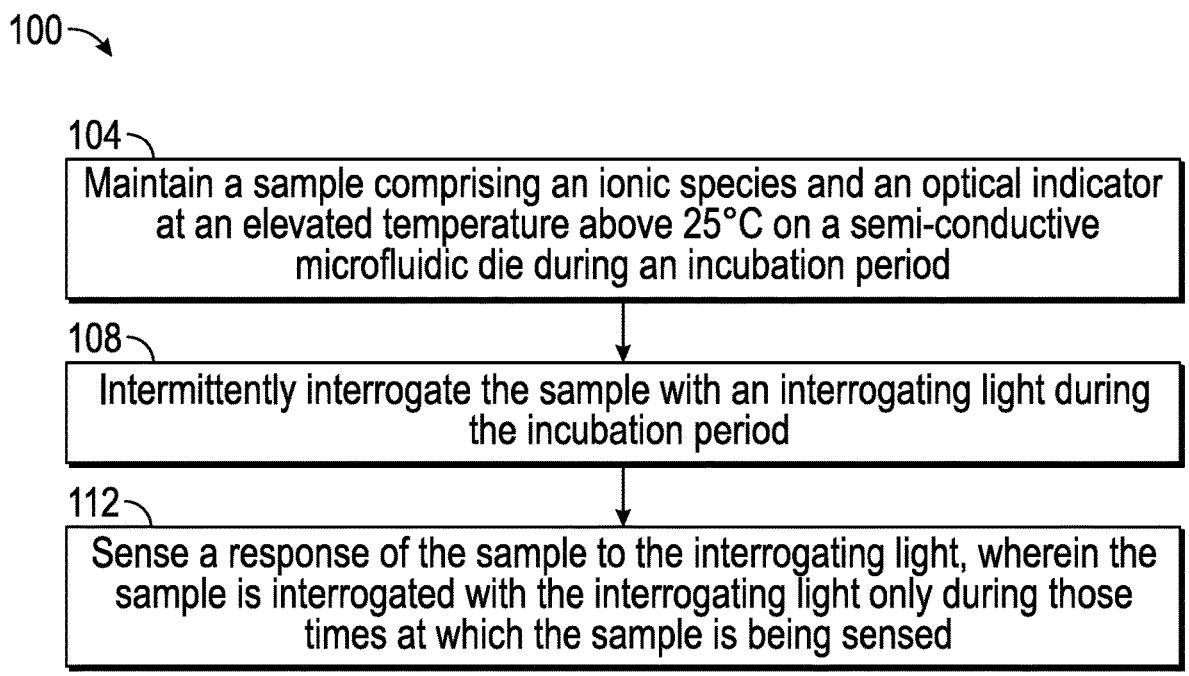
FIG. 2 is a flow diagram of an example method for interrogating and sensing a sample to determine the presence of a targeted ionic species.

FIG. 2 is a flow diagram of an example method 100 for detecting the presence of a targeted ionic species in a sample. Method 100 facilitates the control over the ionic environment of a sample supported by a semiconductive microfluidic die and having an optical indicator for sensing the presence of a targeted ionic species. Although method 100 is described in the context of being carried out using system 20, it should be appreciated that method 100 may be likewise carried out with other systems.

As indicated by block 104, a sample comprising a targeted ionic species 42, the presence of which is to be confirmed and/or measured, and an optical indicator 44 is maintained at an elevated temperature above 25° C. on a semiconductive microfluidic die during an incubation period. The elevated temperature facilitates amplification or multiplication of the targeted ionic species during the incubation period. In some implementations, the sample is maintained at a temperature of up to 110° C., or higher in some applications. In some implementations, although the sample 40 is maintained at a temperature above 25° C. during incubation period, the temperature that is above 25° C. may change as sample 40 undergoes thermal cycling. For example, in some implementations, temperature of the sample may move through several different temperature cycles or phases during the incubation.

In one implementation, sample 40 is maintained at an elevated temperature above 25° C. during an incubation period as part of a polymerase chain reaction (PCR), a molecular biology technology used to amplify a single copy or a few copies of a piece of DNA across several orders of magnitude to generate thousands to millions of copies of the ionic species, such as a particular DNA sequence. During PCR, the sample 40 undergoes thermal cycling, wherein sample 40 is part of a reaction carried out with a series of alternating temperature steps or cycles. The alternating temperature steps or cycles include a denaturing step in which the solution is heated to an elevated temperature (for example, 94 degrees Celsius to 98 degrees Celsius), an annealing step in which the solution is cooled to a lower temperature (for example, 50 degrees Celsius to 65 degrees Celsius) and an extension/elongation step in which the solution is maintained at a temperature between the elevated temperature and the lower temperature (for example, 70 degrees Celsius to 80 degrees Celsius depending upon the DNA polymerase being used). Some polymerase chain reactions additionally comprise an initiation step in the first cycle, a final elongation step during the last cycle and a final hold step if short-term storage is desired.

In one implementation, sample 40 is maintained at an elevated temperature greater than 25° C. as part of a loop mediated isothermal amplification (LAMP) procedure. Unlike a PCR procedure, a LAMP procedure is carried out at a constant temperature. For example, in one implementation, the ionic species 42 of sample 40 may comprise a target DNA or RNA sequence that is amplified/multiplied at a constant temperature of 60 to 65° C. using two or three sets of primers and a polymerase the high strand displacement activity in addition to replication activity. In some implementations, a pair of loop primers may further accelerate the reaction.

In one implementation, microfluidic die 48 with the supported or contained sample 40 is placed within, on, beneath or beside a heating source. For example, in one implementation, microfluidic die 48 with the supported or contained sample 40 may be placed within an oven or on top of a hot plate which is either at the single elevated temperature, such as with a LAMP procedure, or which is cycled through a series of different alternating temperatures, such as with PCR. In one implementation, the heat source may be a heat emitter, such as a heat lamp, that direct heats, such as through convection, onto sample 40 supported by microfluidic die 48. In one implementation where thermal cycling is used, microfluidic die 48 with the supported or contained sample 40 may be moved between different heating sources, different ovens, hot plates or heat emitters, wherein the different ovens, hot plates or heat emitters are themselves at the different temperatures for the different temperature cycles. In some implementations, controller 30 may output control signals controlling the temperature of the heat sources, whether they be an oven, hotplate or lamp.

In some implementations, the heating source that maintains sample 40 at the elevated temperature above 25° (whether a single constant temperature or a changing temperature), may be incorporated into microfluidic die 48. For example, in some implementations, like fluidic die 48 may incorporate embedded electrical resistors that, when conducting electrical current supplied from a power source, emit heat that is thermally conducted to sample 40 within microfluidic die 48. In one implementation, controller 30 may additionally control the heat being output by such a microfluidic die internal heat source. In yet other implementations, a separate controller, distinct from controller 30 may be utilized to control the temperature of sample 40 within microfluidic die 48.

In some implementations, microfluidic die 48 may comprise a temperature sensor or multiple temperature sensors incorporated therein. Such temperature sensors may output signals indicating the temperature of the environment of sample 40 within microfluidic die 48, facilitating close loop feedback control over the temperature. In some implementations, the signals output by such temperature sensors may be transmitted to controller 36 which may utilize such signals not only to control the operation of the single or multiple heat sources, but also control the actuation of light source 22 and sensor 26. In some implementations, such temperature sensors may be omitted.

As indicated by block 108, the sample 40, during the incubation period, is intermittently interrogated with an interrogating light, such as light provided by light source 22. As described above, in one implementation, the light source may be turned on and off by controller 30 to intermittently direct an interrogating light at sample 40 being supported by microfluidic die 48. In another implementation, the light source may be continuously on, wherein a light blocking element, such as a shutter, is alternated between a light blocking and a light transmissive state.

As indicated by block 112, a response of the sample to the interrogating light is sensed, wherein the sample is interrogated with the interrogating light only during those times at which the sample is being sensed. In contrast to the sample 40 being impinged with light from light source 22 continuously during the incubation period, the sample 40 and the supporting microfluidic die 48 are only impinged with light, with interrogating light from light source 22, during those specific time periods at which the optical response of sample 40 to the interrogating light is actually being sensed. In other words, the sample 40 and the supporting microfluidic die 48 are only impinged with light from light source 22 when sensor 26 is taking actual readings regarding the optical response of sample 42 such interrogating light. At other times, light source 22 is either turned off by controller 30 or is blocked such that light from light source 22 cannot impinge sample 40 and microfluidic die 48. As discussed above, the reduced exposure of sample 40 and microfluidic die 48 to light from light source 22 reduces free electrons to provide a more stable and controlled ionic environment for sample 40 during testing.

In one example implementation of method 100, a test may be carried out to indicate the presence or absence of nucleic acid in a sample 40. In the example implementation, sample 40 may be located in a microfluidic volume 50 of a silicon microfluidic die 48, wherein the sample at a size of 1 picoliter to 10 µL The sample 40 may include an optical indicator in the form of a fluorophore, Calcein. The sample 40 may additionally include the quenching ions associated with Calcein ($Mn^{2+}$, $Fe^{2+}$, $Fe^{3+}$, $Co^{2+}$, $Ni^{2+}$ or $Cu^{2+}$) and LAMP reaction catalysts or reagents as part of a LAMP procedure. Calcein fluorescence intensity is diminished significantly in the presence of a quenching ion. The ionic byproducts of successful nucleic acid (DNA) amplification/multiplication include high concentrations of pyrophosphate ions (PPi) which attract the quenching ions away from Calcein, causing Calcein to fluoresce brightly.

During the LAMP procedure, sample 40 may be detained at a temperature of between 58° C. and 65° C. Light source 22 may apply an interrogating light to the sample 40, the interrogating light having a wavelength of 400 nm (near ultraviolet) to 480 nm (blue visible light). The light maybe pulsed at a frequency coinciding with image capture or sensing by sensor 26. In one implementation, like may be pulsed at intervals ranging from less than one second to 10 minutes. Reducing the size of such intervals at which the light from light source 22 is pulsed may provide enhanced real-time detection of a nucleic acid test reaction, which indicates the presence of the ionic species, nucleic acid (DNA). The intermittent interrogation of the sample 40 with the excitation light from light source 22 maintains enhanced control over the ionic environment of sample 40, enhancing the reliability and accuracy of the test with fewer false positives and fewer false negatives as compared to identical tests where light source 22 continuously applies an interrogating light to sample 40 during the same LAMP procedure.

Figure 3:
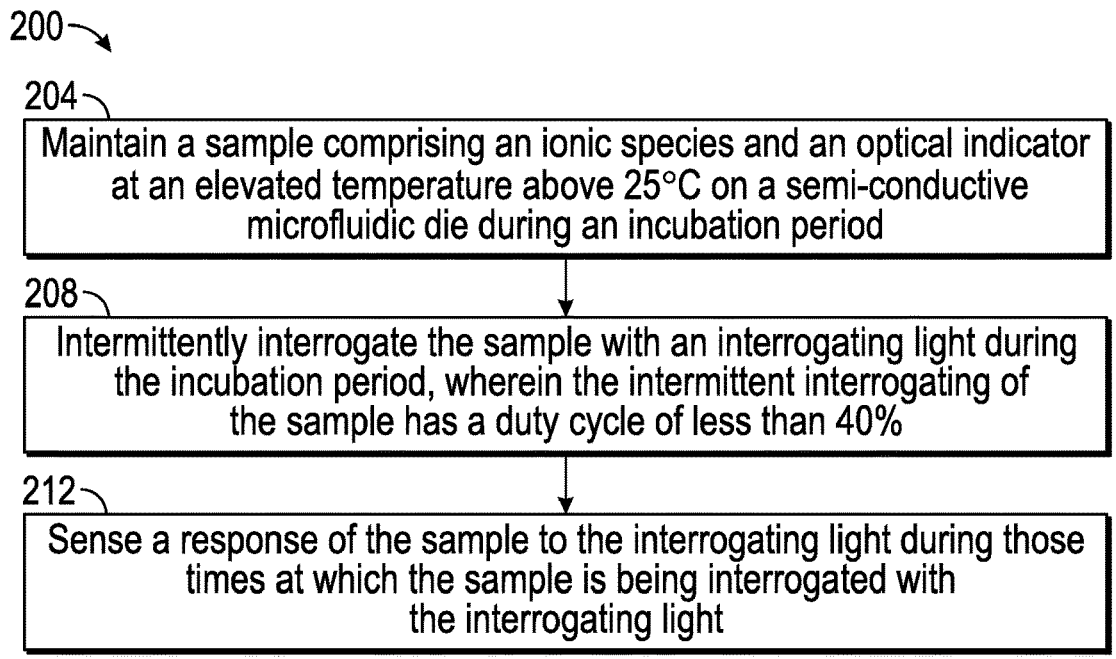
FIG. 3 is a flow diagram of an example method for interrogating and sensing a sample to determine the presence of a targeted ionic species.

FIG. 3 is a flow diagram of another example method for detecting the presence of a targeted ionic species in a sample. Method 200 facilitates the control over the ionic environment of a sample supported by a semiconductive microfluidic die and having an optical indicator for sensing the presence of a targeted ionic species. Although method 200 is described in the context of being carried out using system 20, it should be appreciated that method 200 may be likewise carried out with other systems.

As indicated by block 204, a sample comprising a targeted ionic species 42, the presence of which is to be confirmed and/or measured, and an optical indicator 44 is maintained at an elevated temperature above 25° C. on a semiconductive microfluidic die during an incubation period. The elevated temperature facilitates amplification or multiplication of the targeted ionic species during the incubation period. In some implementations, the sample is maintained at a temperature of up to 110° C., or higher in some applications. In some implementations, although the sample 40 is maintained at a temperature above 25° C. during incubation period, the temperature that is above 25° C. may change as sample 40 undergoes thermal cycling. For example, in some implementations, temperature of the sample may move through several different temperature cycles or phases during the incubation.

In one implementation, sample 40 is maintained at an elevated temperature above 25° C. during an incubation period as part of a polymerase chain reaction (PCR), a molecular biology technology used to amplify a single copy or a few copies of a piece of DNA across several orders of magnitude to generate thousands to millions of copies of the ionic species, such as a particular DNA sequence. During PCR, the sample 40 undergoes thermal cycling, wherein sample 40 is part of a reaction carried out with a series of alternating temperature steps or cycles. The alternating temperature steps or cycles include a denaturing step in which the solution is heated to an elevated temperature (for example, 94 degrees Celsius to 98 degrees Celsius), an annealing step in which the solution is cooled to a lower temperature (for example, 50 degrees Celsius to 65 degrees Celsius) and an extension/elongation step in which the solution is maintained at a temperature between the elevated temperature and the lower temperature (for example, 70 degrees Celsius to 80 degrees Celsius depending upon the DNA polymerase being used). Some polymerase chain reactions additionally comprise an initiation step in the first cycle, a final elongation step during the last cycle and a final hold step if short-term storage is desired.

In one implementation, sample 40 is maintained at an elevated temperature greater than 25° C. as part of a loop mediated isothermal amplification (LAMP) procedure. Unlike a PCR procedure, a LAMP procedure is carried out at a constant temperature. For example, in one implementation, the ionic species 42 of sample 40 may comprise a target DNA or RNA sequence that is amplified/multiplied at a constant temperature of 60 to 65° C. using two or three sets of primers and a polymerase the high strand displacement activity in addition to replication activity. In some implementations, a pair of loop primers may further accelerate the reaction.

In one implementation, microfluidic die 48 with the supported or contained sample 40 is placed within, on, beneath or beside a heating source. For example, in one implementation, microfluidic die 48 with the supported or contained sample 40 may be placed within an oven or on top of a hot plate which is either at the single elevated temperature, such as with a LAMP procedure, or which is cycled through a series of different alternating temperatures, such as with PCR. In one implementation, the heat source may be a heat emitter, such as a heat lamp, that direct heats, such as through convection, onto sample 40 supported by microfluidic die 48. In one implementation where thermal cycling is used, microfluidic die 48 with the supported or contained sample 40 may be moved between different heating sources, different ovens, hot plates or heat emitters, wherein the different ovens, hot plates or heat emitters are themselves at the different temperatures for the different temperature cycles. In some implementations, controller 30 may output control signals controlling the temperature of the heat sources, whether they be an oven, hotplate or lamp.

In some implementations, the heating source that maintains sample 40 at the elevated temperature above 25° (whether a single constant temperature or a changing temperature), may be incorporated into microfluidic die 48. For example, in some implementations, like fluidic die 48 may incorporate embedded electrical resistors that, when conducting electrical current supplied from a power source, emit heat that is thermally conducted to sample 40 within microfluidic die 48. In one implementation, controller 30 may additionally control the heat being output by such a microfluidic die internal heat source. In yet other implementations, a separate controller, distinct from controller 30 may be utilized to control the temperature of sample 40 within microfluidic die 48.

In some implementations, microfluidic die 48 may comprise a temperature sensor or multiple temperature sensors incorporated therein. Such temperature sensors may output signals indicating the temperature of the environment of sample 40 within microfluidic die 48, facilitating close loop feedback control over the temperature. In some implementations, the signals output by such temperature sensors may be transmitted to controller 36 which may utilize such signals not only to control the operation of the single or multiple heat sources, but also control the actuation of light source 22 and sensor 26. In some implementations, such temperature sensors may be omitted.

As indicated by block 208, the sample 40, during the incubation period, is intermittently interrogated with an interrogating light, such as light provided by light source 22. As described above, in one implementation, the light source may be turned on and off by controller 30 to intermittently direct an interrogating light at sample 40 being supported by microfluidic die 48. In another implementation, the light source may be continuously on, wherein a light blocking element, such as a shutter, is alternated between a light blocking and a light transmissive state. The intermittent interrogating of the sample 40 has a duty cycle of less than 40% during the incubation period of time during which the ionic species is being amplified or multiplied. In other words, powering of light source 22 or the actuation of a light blocking element or shutter may be pulsed or cycled between on/off or light blocking/light transmitting states, wherein sample 40 and microfluidic die 48 are interrogated or impinged with light from light source 22 up to 40% of the time during which the ionic species is being amplified or multiplied.

As indicated by block 212, a response of the sample to the interrogating light is sensed during those times at which the sample is being interrogated with the interrogating light. As discussed above, the reduced exposure of sample 40 and microfluidic die 48 to light from light source 22 reduces free electrons to provide a more stable and controlled ionic environment for sample 40 during testing.

Figure 4:
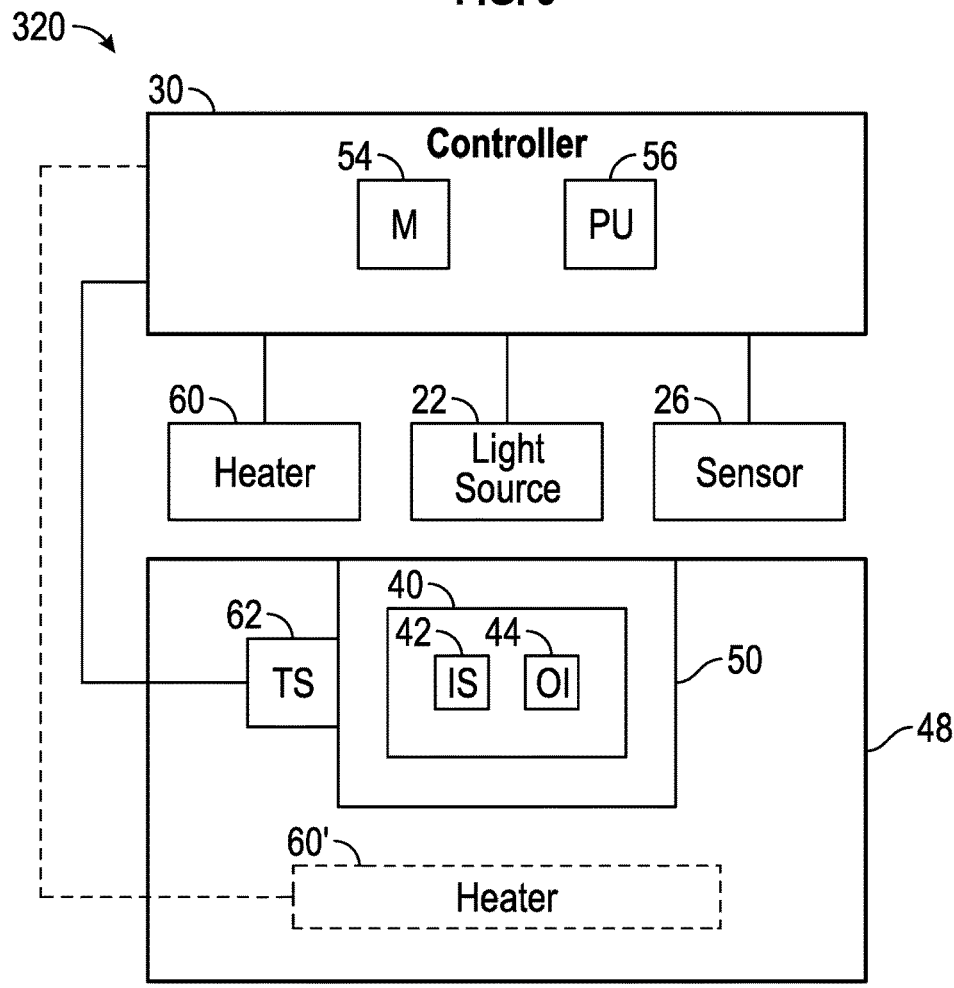
FIG. 4 is a schematic diagram of portions of an example ionic species interrogation and sensing system.

FIG. 4 schematically illustrates portions of another example ionic species interrogation and sensing system 320. As a system 20, system 320 facilitates the provision of a controlled ionic environment for testing for the presence of an ionic species, such as a nucleic acid, in a sample supported on a microfluidic die. System 320 is similar to system 20 except that system 320 is illustrated as additionally comprising heater 60 and temperature sensor 62. Those remaining components or elements of system 320 which correspond to components or elements of system 20 are numbered similarly.

Heater 62 comprises a device to maintain sample 40 within or on microfluidic device 48 at an elevated temperature above 25° C. during an incubation period. The elevated temperature facilitates amplification or multiplication of the targeted ionic species during the incubation period. In some implementations, the sample is maintained at a temperature of up to 110° C., or higher in some applications. In some implementations, although the sample 40 is maintained at a temperature above 25° C. during the incubation period, the temperature that is above 25° C. may change as sample 40 undergoes thermal cycling. For example, in some implementations, temperature of the sample may move through several different temperature cycles or phases during the incubation.

Heater 60 operates under the control of controller 30. In one implementation, sample 40 is maintained at an elevated temperature above 25° C. during an incubation period as part of a polymerase chain reaction (PCR), a molecular biology technology used to amplify a single copy or a few copies of a piece of DNA across several orders of magnitude to generate thousands to millions of copies of the ionic species, such as a particular DNA sequence. During PCR, the sample 40 undergoes thermal cycling, wherein sample 40 is part of a reaction carried out with a series of alternating temperature steps or cycles. The alternating temperature steps or cycles include a denaturing step in which the solution is heated to an elevated temperature (for example, 94 degrees Celsius to 98 degrees Celsius), an annealing step in which the solution is cooled to a lower temperature (for example, 50 degrees Celsius to 65 degrees Celsius) and an extension/elongation step in which the solution is maintained at a temperature between the elevated temperature and the lower temperature (for example, 70 degrees Celsius to 80 degrees Celsius depending upon the DNA polymerase being used). Some polymerase chain reactions additionally comprise an initiation step in the first cycle, a final elongation step during the last cycle and a final hold step if short-term storage is desired.

In one implementation, controller 30 controls heater 60 to maintain sample 40 at an elevated temperature greater than 25° C. as part of a loop mediated isothermal amplification (LAMP) procedure. Unlike a PCR procedure, a LAMP procedure is carried out at a constant temperature. For example, in one implementation, the ionic species 42 of sample 40 may comprise a target DNA or RNA sequence that is amplified/multiplied at a constant temperature of 60 to 65° C. using two or three sets of primers and a polymerase the high strand displacement activity in addition to replication activity. In some implementations, a pair of loop primers may further accelerate the reaction.

In one implementation, heater 60 receives or is beneath or beside a microfluidic die 48 and the supported sample 40. For example, in one implementation, microfluidic die 48 with the supported or contained sample 40 may be placed within an oven or on top of a hot plate which is either at the single elevated temperature, such as with a LAMP procedure, or which is cycled through a series of different alternating temperatures, such as with PCR. In one implementation, heater 60 may comprise a heat emitter, such as a heat lamp, that directs heat, such as through convection, onto sample 40 supported by microfluidic die 48. In one implementation where thermal cycling is used, heater 60 may comprise multiple heating stations, wherein microfluidic die 48 with the supported or contained sample 40 may be moved between the different heating stations and wherein the different ovens, hot plates or heat emitters are themselves at the different temperatures for the different temperature cycles.

As shown in broken lines, in some implementations, a heater 60' may be incorporated into microfluidic die 48 and may be operable under the control of controller 30. For example, in some implementations, microfluidic die 48 may incorporate embedded electrical resistors that, when conducting electrical current supplied from a power source, emit heat that is thermally conducted to sample 40 within microfluidic die 48.

Temperature sensor 62 comprises a temperature sensing element or multiple temperature sensing elements incorporated into microfluidic die 48. Such temperature sensors may output signals indicating the temperature of the environment of sample 40 within microfluidic die 48, facilitating close loop feedback control over the temperature by controller 30. In some implementations, the signals output by such temperature sensors may be transmitted to controller 36 which may utilize such signals not only to control the operation of heat source 60, but to also control the actuation of light source 22 and sensor 26. In some implementations, such temperature sensors may be omitted.

Figure 5:
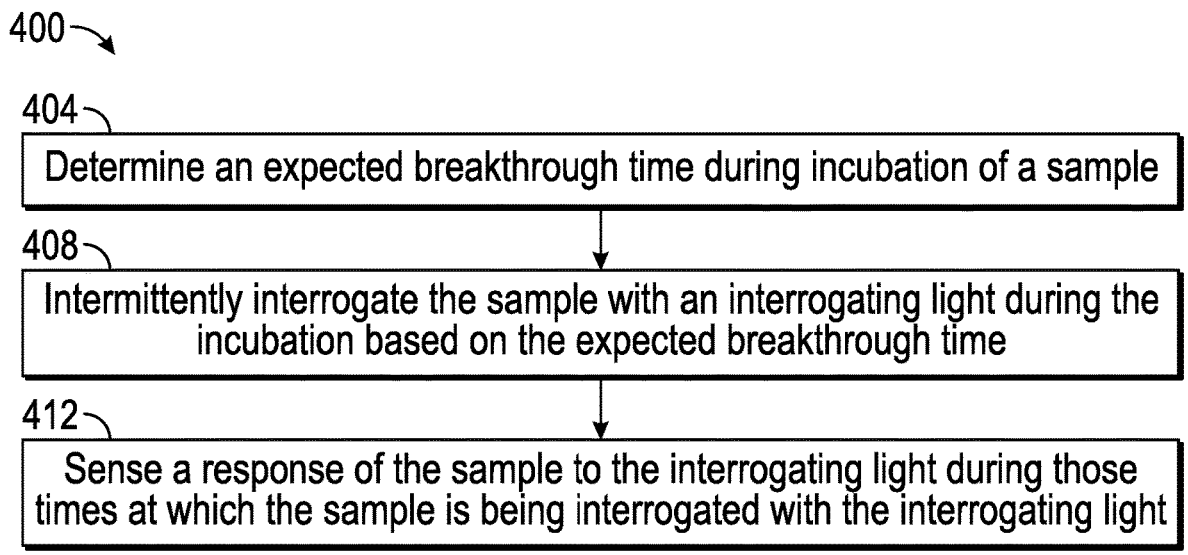
FIG. 5 is a flow diagram of an example method for interrogating and sensing a sample to determine the presence of a targeted ionic species.

FIG. 5 is a flow diagram of an example method 400 for detecting the presence of a targeted ionic species in a sample. Method 400 facilitates the control over the ionic environment of a sample supported by a semiconductive microfluidic die being tested for the presence of a targeted ionic species. Although method 400 is described in the context of being carried out using system 20, it should be appreciated that method 400 may be likewise carried out with other systems, such as system 320 or similar systems.

As indicated by block 404, an expected breakthrough time of the sample during incubation is determined or estimated. The expected breakthrough time is an expected or predicted point in time during the period of incubation at which the ionic species, if present, will have been multiplied or amplified to a sufficient extent so as to produce an optical response upon being interrogated that exceeds a predefined threshold used to indicate the presence of the ionic species in the sample.

The actual time during the period of incubation for the sample at which the optical response of the sample achieves breakthrough, exceeding the threshold, may often indicate not only the presence or absence of the targeted ionic species, but also in extent or degree to which the ionic species may be present in the sample, and present in the host from which the sample was taken. For example, a sample which achieves "breakthrough" earlier may be determined to have a greater extent of the targeted ionic species as compared to a different sample which achieves the same breakthrough later in time during the incubation period. Of course, sample which is not achieved breakthrough may be determined to not contain the targeted ionic species.

The determination or prediction for the expected breakthrough time may be made based upon multiple factors such as the multiplication or amplification process being utilized, the temperature cycle or cycles being utilized, the targeted isotope for which the presence is being tested, the optical indicator being used and the reaction catalyst, if any, for multiplying the ionic species. In one implementation, controller 30 makes such a determination based upon inputs received by controller 30. In another implementation, the expected breakthrough time is input to controller 30 or is retrieved by controller 30 from a database or other data source.

As indicated by block 408, the sample, such a sample 40, is intermittently interrogated with interrogating light during the incubation based upon the expected breakthrough time. In one implementation, the sensing of the optical response to the interrogating light is also correspondingly intermittent. In such an implementation, the frequency at which the sample is intermittently interrogated with light to produce the optical response, based in part upon the optical indicator, is varied based upon the predetermined anticipated or expected breakthrough time. For example, during a window of time containing the expected breakthrough time, the sample may be interrogated with light at a first frequency that is greater than a second frequency at which the sample is interrogated at other times outside the window. In another implementation, the frequency at which the sample is intermittently interrogated with light from light source 22 may increase as the expected breakthrough time for the target analyte is approached.

As indicated by block 412, a response of the sample to the interrogating light is sensed during those times at which the sample is being interrogated with the interrogating light. In one implementation, a sensor, such as sensor 26, is controlled so as to also intermittently sense sample 40 at the same frequency at which the sample is presently in being interrogated with interrogating light. As with the frequency of the interrogating light, the frequency at which the sample is intermittently sensed is also varied based upon the predetermined anticipated or expected breakthrough time. For example, during a window of time containing the expected breakthrough time, the sample may be sensed at a first frequency that is greater than a second frequency at which the sample is sensed at other times outside the window. In another implementation, the frequency at which the sample is intermittently sensed may increase as the expected breakthrough time for the target analyte is approached.

By interrogating the sample with light at a greater frequency during the window of time containing the expected breakthrough time, a greater resolution for the actual breakthrough time may be achieved. At the same time, by interrogating the sample with light at the lower first frequency during those interrogation times outside of the window, the sample, and the microfluidic die supporting the sample, are subjected to less light, reducing the number of free electrons that may be produced by the semiconductive material and providing more stability or control over the ionic environment of the sample being tested.

Figure 6:
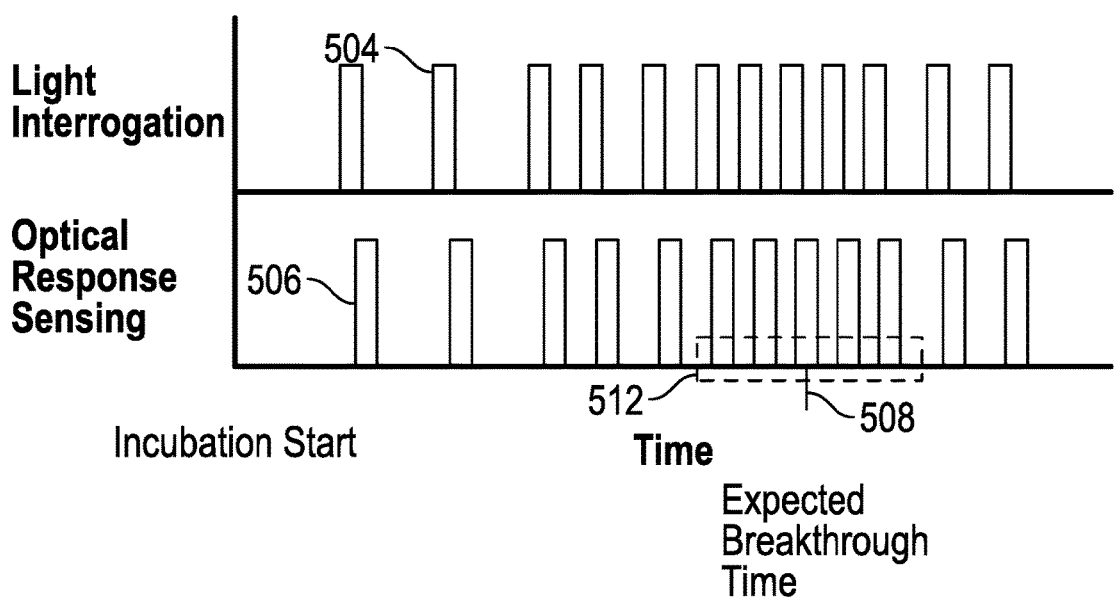
FIG. 6 is a diagram illustrating an example method for interrogating and sensing a sample to determine the presence of a targeted ionic species.

FIG. 6 illustrates one example implementation of method 400. FIG. 6 is a diagram illustrating light interrogation and optical response sensing of a sample 40 by system 20 (or system 320) during an incubation period in which the sample is maintained at an elevated temperature to amplifier multiply a targeted ionic species 42, if present. Vertical bars 504 represent the timing and duration of the individual light interrogation events of sample 40 during the incubation of sample 40 starting from the initiation of the incubation period. Vertical bars 506 represent the timing and duration of the individual optical response sensing events of sample 40 starting from the initiation of the incubation period. The height of the vertical bars 504, 506 does not indicate amplitude or intensity.

In the example illustrated, the frequency of light interrogation events 504 increases as the expected breakthrough time 508 approaches during the incubation of sample 40. Likewise, the corresponding frequency of the optical response sensing events also increases as the expected breakthrough time 508 approaches during the incubation of sample 40. In the example illustrated, each sensing event 506 corresponds to a corresponding light interrogation event 504, but is slightly delayed in time. In other implementations, each sensing event 506 may identically correspond in time to a corresponding light interrogation event.

In the particular example illustrated, the frequency of the light interrogation events 504 as well as the frequency of the corresponding optical response sensing events 506 have a first frequency during a window of time 512 containing the expected breakthrough time 508 for the sample 40 and a second frequency, less than the first frequency, outside the window of time 512. As a result, the frequency of the light interrogation events 504 and the frequency of the optical response sensing events 506 decreases past the window of time 512. In other implementations, the frequency of the light interrogation events 504 and the frequency of the optical response sensing events 506 may be maintained at the same frequency following the window of time 512 as during the window of time 512. In some implementations, the frequency of the light interrogation events 504 and the frequency of the optical response sensing events 506 may be increased during the window of time 512 or following the window of time 512.

Figure 7:
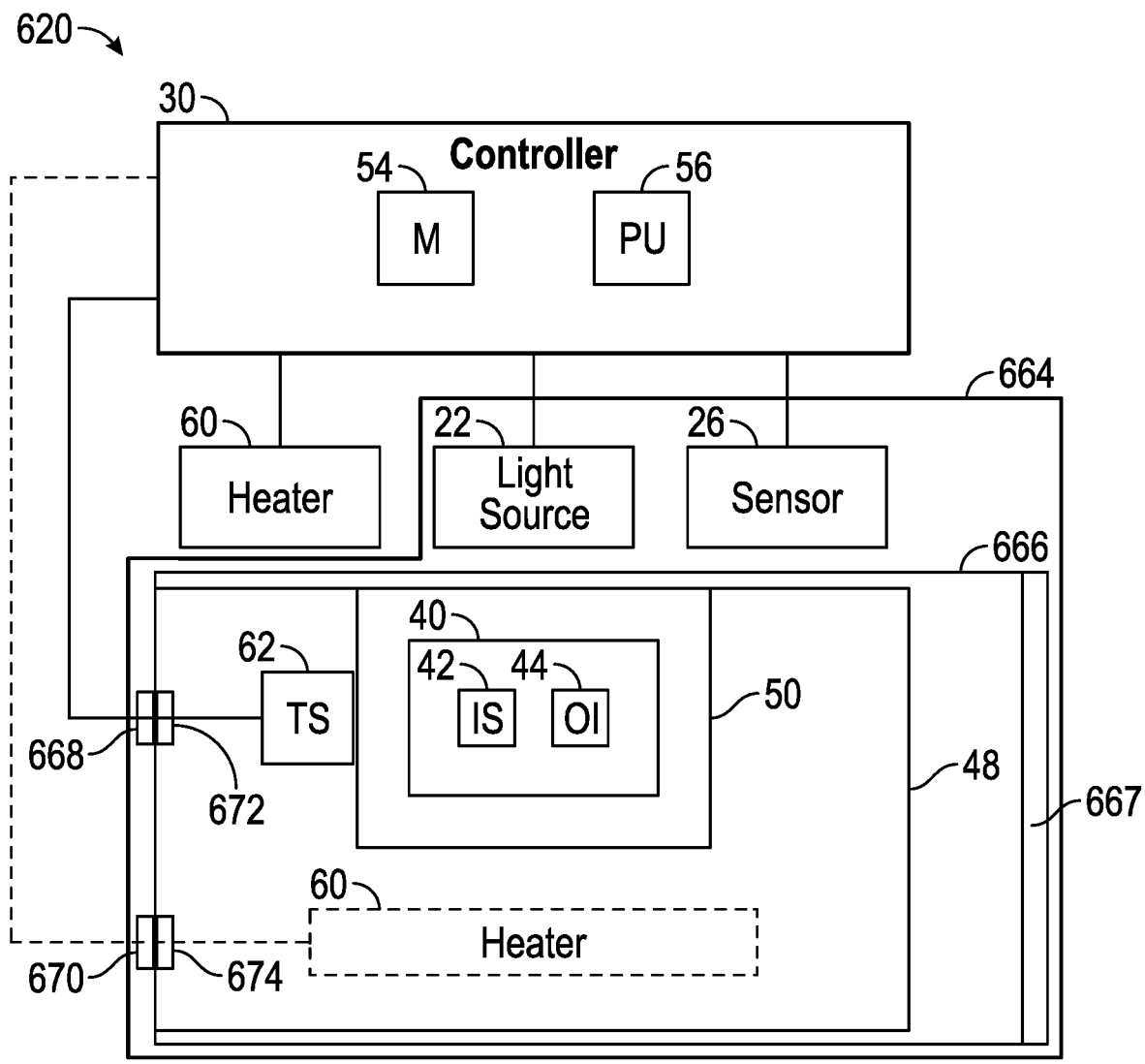
FIG. 7 is a schematic diagram of portions of an example ionic species interrogation and sensing system.

FIG. 7 is a schematic diagram of portions of an example ionic species interrogation and sensing system 620. System 620 is similar to system 320 described above except that system 620 provides further enhanced control over the ionic environment of the sample being tested by further inhibiting ambient light from impinging the semiconductive microfluidic die and the contained sample. System 620 additionally comprises light blocking enclosure 664. Those remaining components of system 620 which correspond to components of system 320 are numbered similarly.

Light blocking enclosure 664 encloses microfluidic die 48 and contained sample 40, positioning and supporting chamber 50 and sample 40 in proximity with light source 22 and sensor 26 such that sample 40 may be interrogated with light from light source 22 and such as sensor 26 may sense the response of sample 42 such interrogation. Life blocking enclosure 664 is sufficiently opaque so as to block ambient light that may interact with the semiconductive material of microfluidic die 48 to form free electrons that may alter the ionic environment of sample 40. Enclosure 664 permits light from light source 22 to reach sample 40 and chamber 50 and further enables sensors 26 to sense the response of sample 40 to such intermittent interrogating light.

To facilitate reuse of enclosure 664, enclosure 664 comprise a die receiving chamber 666 having an access door 667 which may be opened and closed, wherein access door 667 facilitates insertion of microfluidic die 48 into chamber 666 and withdrawal of microfluidic die 48 from chamber 666. In the example illustrated, chamber 666 additionally comprises electrical interfaces 668, 670 which automatically align and electrically contact corresponding electrical interfaces 672, 674 on microfluidic die 48 when microfluidic die 48 is inserted into chamber 666 and guided by internal guiding structures of chamber 666. In one implementation, such interfaces 668, 672; 670, 672 may comprise paired contact pins and contact sockets. In other implementations, such interfaces may have other forms. Such interfaces facilitate automatic connection of controller 30 to temperature sensor 62 and heater 60, when provided. In other implementations, such interfaces may be omitted, such as where other mechanisms are provided for connecting temperature sensor 62 and/or heater 60 to controller 30 or heater 60 and/or temperature sensor 62 are omitted from microfluidic die 48.

Figure 8:
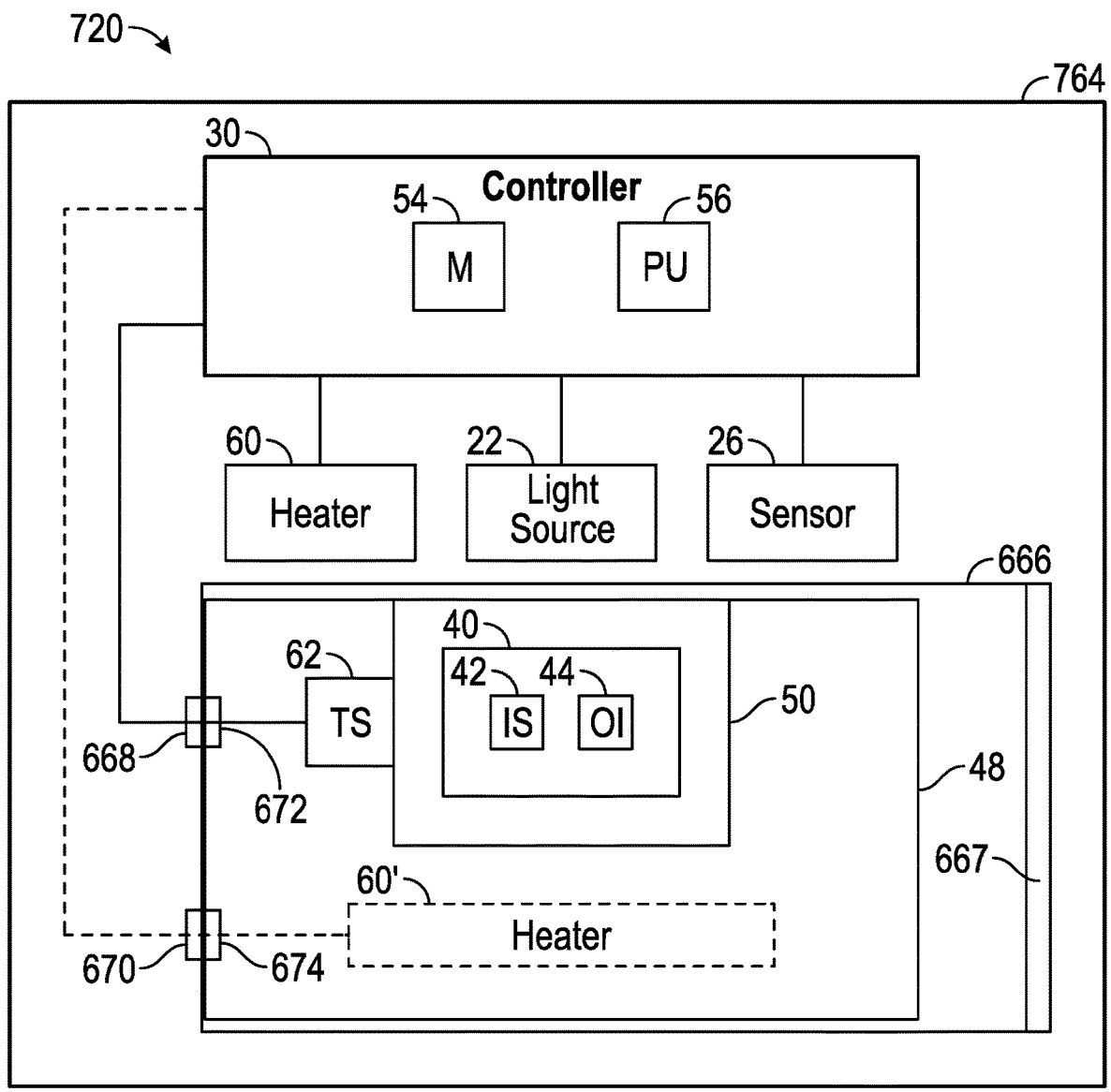
FIG. 8 is a schematic diagram of portions of an example ionic species interrogation and sensing system.

FIG. 8 is a schematic diagram of portions of an example ionic species interrogation and sensing system 720. System 720 is similar to system 620 described above except that system 720 comprises light blocking enclosure 764 in place of light blocking enclosure 664. Those remaining components of system 720 which correspond to components of system 620 are numbered similarly.

Light blocking enclosure 764 is similar to light blocking enclosure 664 except that light blocking closures 764 additionally encloses controller 30 and heater 60 (when heater 60 is not provided as part of microfluidic die 48). Life blocking enclosure 764 is sufficiently opaque so as to block ambient light that may interact with the semiconductive material of microfluidic die 48 to form free electrons that may alter the ionic environment of sample 40. Enclosure 764 permits light from light source 22 to reach sample 40 and chamber 50 and further enables sensors 26 to sense the response of sample 40 to such intermittent interrogating light.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. A method comprising:
   maintaining a sample comprising an ionic species and an optical indicator at an elevated temperature above 25° C. on a semi-conductive microfluidic die during an incubation period;
   intermittently interrogating the sample with an interrogating light during the incubation period, wherein the intermittent interrogation of the sample with the interrogating light has a varying frequency during the incubation period; and
   sensing a response of the sample to the interrogating light, wherein the sample is interrogated with the interrogating light only during those times at which the sample is being sensed.

2. The method of claim 1, wherein the intermittent interrogating of the sample has a duty cycle of less than 40%.

3. The method of claim 1, wherein the intermittent interrogating of the sample has a duty cycle of less than 10%.

4. The method of claim 1, wherein the ionic species comprises a nucleic acid.

5. The method of claim 1, wherein the optical indicator comprises a fluorophore.

6. The method of claim 1, wherein the optical indicator comprises a dye.

7. The method of claim 1, wherein the maintaining of the sample at the elevated temperature above 25° C. comprises cycling the sample through a plurality of different elevated temperatures above 25° C.

8. The method of claim 1, wherein optical indicator comprises a fluorophore and wherein the intermittent interrogation of the sample with the interrogating light has a first frequency during a window of time containing an expected fluorescence breakthrough time for the sample and a second frequency, less than the first frequency outside the window.

9. The method of claim 1, further comprising enclosing the semi-conductive microfluidic die, the light source and the sample in a light blocking enclosure.

10. The method claim 1, wherein intermittently interrogating the sample includes pulsing or cycling the interrogating light on and off during the incubation period.

11. A method comprising:
    maintaining a sample comprising an ionic species and an optical indicator at an elevated temperature above 25° C. on a semi-conductive microfluidic die during an incubation period;
    intermittently interrogating the sample with an interrogating light during the incubation period by pulsing the interrogating light a plurality of times during the incubation period, wherein each pulse of the plurality of pulses includes turning the interrogating light on and off during the incubation period, wherein the intermittent interrogating of the sample has a duty cycle of less than 40%, and wherein the intermittent interrogating the sample with the interrogating light includes using a varying frequency during the incubation period; and
    sensing a response of the sample to the interrogating light during those times at which the sample is being interrogated with the interrogating light.

12. The method of claim 11, wherein the intermittent interrogating of the sample has a duty cycle of less than 10%.

13. The method of claim 11, wherein the incubation period includes a period of time during which the sample is at an elevated temperature and in a presence of a reaction catalyst.

14. The method of claim 11, wherein the intermittent interrogation of the sample begins at a predefined time following initiation of the incubation period.

15. The method of claim 11, wherein intermittently interrogating the sample with the interrogating light continues until an optical response of the sample during the incubation period satisfies a predetermined threshold.

* * * * *